United States Patent
Tsujii et al.

(10) Patent No.: US 8,488,742 B2
(45) Date of Patent: Jul. 16, 2013

(54) X-RAY GENERATOR, X-RAY IMAGING APPARATUS, AND CONTROL METHODS THEREFOR

(75) Inventors: Osamu Tsujii, Kawasaki (JP); Makoto Sato, Tokyo (JP); Masahiko Okunuki, Akiruno (JP); Satoshi Shimizu, Great Neck, NY (US); Takashi Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 391 days.

(21) Appl. No.: 12/745,437

(22) PCT Filed: Feb. 4, 2009

(86) PCT No.: PCT/JP2009/051853
§ 371 (c)(1),
(2), (4) Date: May 28, 2010

(87) PCT Pub. No.: WO2009/101882
PCT Pub. Date: Aug. 20, 2009

(65) Prior Publication Data
US 2010/0310051 A1 Dec. 9, 2010

(30) Foreign Application Priority Data
Feb. 13, 2008 (JP) ................. 2008-032351

(51) Int. Cl.
*H01J 35/14* (2006.01)
(52) U.S. Cl.
USPC ........................................ 378/138
(58) Field of Classification Search
USPC ............... 378/119, 136–138, 143, 145
See application file for complete search history.

(56) References Cited

U.S. PATENT DOCUMENTS

| 4,866,749 A | 9/1989 | Uematu |
| 5,566,220 A | 10/1996 | Saito et al. |
| 2002/0126798 A1 | 9/2002 | Harris et al. |
| 2004/0114721 A1* | 6/2004 | Qiu et al. ............... 378/122 |

FOREIGN PATENT DOCUMENTS

| CN | 1833299 A | 9/2006 |
| JP | 06-013195 A | 1/1994 |
| JP | 08-264139 A | 10/1996 |
| JP | 09-180894 A | 7/1997 |
| JP | 2003-100242 A | 4/2003 |
| JP | 2005-237779 A | 9/2005 |
| JP | 2007-504636 A | 3/2007 |
| WO | 2007/100105 A | 9/2007 |

OTHER PUBLICATIONS

Freeman et al., "The design and use of steerable filters", IEEE Trans. Pattern Analysis and Machine Intelligence, vol. 13 No. 9, pp. 891-906, 1991.
Office Action issued on Oct. 26, 2012 in counterpart Chinese Application No. 200980104566.6.

* cited by examiner

*Primary Examiner* — Irakli Kiknadze
(74) *Attorney, Agent, or Firm* — Carter, DeLuca, Farrell & Schmidt LLP

(57) ABSTRACT

In an X-ray generator which includes an electron beam generating unit which has a plurality of electron emitters and generates an electron beam corresponding to driven electron emitters, and a target electrode which generates X-rays with the irradiation position of an electron beam generated by the electron beam generating unit being an X-ray focus, the X-ray focus shape formed by a set of X-ray focuses on the target electrode is controlled by individually controlling driving of the plurality of electron emitters.

20 Claims, 9 Drawing Sheets

F I G. 4
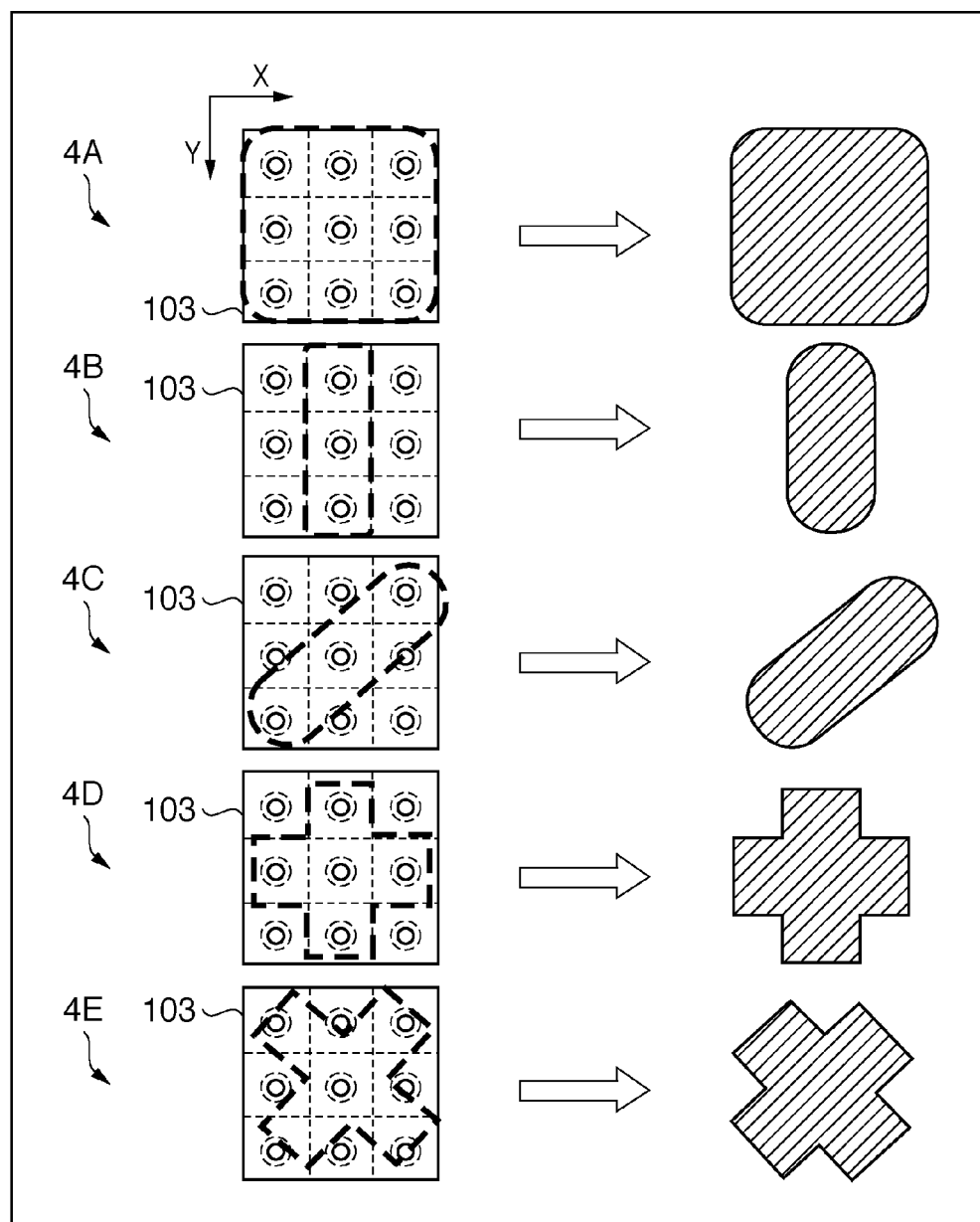

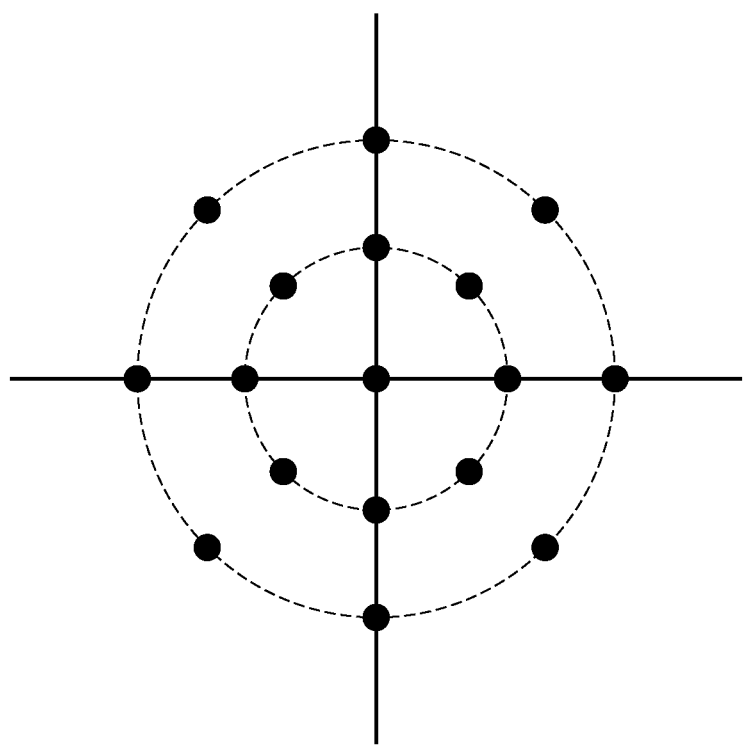
F I G. 9

X-RAY GENERATOR, X-RAY IMAGING APPARATUS, AND CONTROL METHODS THEREFOR

CROSS REFERENCE TO RELATED APPLCIATIONS

This application is a U.S. National Stage of International application No. PCT/JP2009 /051853 filed on Feb. 4, 2009 which claims priority from Japanese Patent Application No. 2008-032351 filed on Feb. 13, 2008, the disclosures of which are hereby incorporated by reference herein in their entirety.

TECHNICAL FIELD

The present invention relates to an X-ray generator used for nondestructive X-ray imaging in the fields of medical diagnosis equipment and industrial equipment using X-ray sources and an X-ray imaging apparatus using the X-ray generator.

BACKGROUND ART

In general, an X-ray tube uses a thermoelectron source as an electron source, forms a desired electron beam by accelerating and focusing thermoelectrons emitted from a filament heated to a high temperature, and generates X-rays by irradiating an X-ray target made of a metal with the electron beam.

Recently, there have been developed, as an electron source replacing this thermoelectron source, a Spint-type electron source which extracts electrons by applying high electric fields to the tips of fine needles or a cold cathode type electron source using carbon nanotubes and the like. As these applications of these techniques, techniques of extracting a single electron beam are described in patent references 1, 2, and 3:

Patent Reference 1: Japanese Patent Laid-Open No. 08-264139

Patent Reference 2: Japanese Patent Laid-Open No. 09-180894

Patent Reference 3: Japanese Patent Laid-Open No. 2005-237779

It is known that when X-rays are generated by irradiating a target with an accelerated electron beam, the generation efficiency of X-rays is very low. Most of the energy of an electron beam applied to the target is converted into heat. For this reason, a conventional X-ray generator uses a rotating anode structure in which a target is rotated.

In a structure in which an electron beam irradiation surface faces an X-ray generation surface as described in patent reference 1, it is difficult to use a rotating anode which suppresses the generation of heat as described in patent reference 3.

Medical diagnosis equipment or the like requires a certain amount of current to secure image quality necessary for diagnosis. In order to obtain high sharpness for an image, it is preferable that the size of X-ray focus formed on a target be small. However, as the size of an X-ray focus is decreased while a certain amount of current is secured, a heat load is focused on a small area, thus causing the above problem of the generation of heat. On the other hand, as the size of an X-ray focus is increased, the sharpness decreases.

It is an object of the present invention to provide an X-ray generator and X-ray imaging apparatus which achieve a large current in the generation of X-rays without decreasing the sharpness of an image.

SUMMARY OF THE INVENTION

In order to achieve the above object, an X-ray generator according to an aspect of the present invention has the following arrangement. That is, the apparatus comprises electron beam generating means, having a plurality of electron emitters, for generating an electron beam corresponding to driven electron emitters, a target electrode which generates X-rays with an irradiation position of an electron beam generated by the electron beam generating means being an X-ray focus, and driving control means for controlling an X-ray focus shape formed by a set of X-ray focuses on the target electrode by individually controlling driving of the plurality of electron emitters.

In order to achieve the above object, an X-ray imaging apparatus according to another aspect of the present invention has the following arrangement. That is, the apparatus comprises electron beam generating means, having a plurality of electron emitters, for generating an electron beam corresponding to driven electron emitters, a target electrode which generates X-rays with an irradiation position of an electron beam generated by the electron beam generating means being an X-ray focus, driving control means for controlling an X-ray focus shape formed by a set of X-ray focuses on the target electrode by individually controlling driving of the plurality of electron emitters, detection means for generating a two-dimensional X-ray image by detecting X-rays generated from the target electrode, and determination means for determining the X-ray focus shape which the driving control means is to form on the target electrode, based on the two-dimensional X-ray image detected by the detection means.

According to the present invention, there are provided an X-ray generator and X-ray imaging apparatus which achieve a large current in the generation of X-rays without decreasing the sharpness of an image.

Other features and advantages of the present invention will be apparent from the following description taken in conjunction with the accompanying drawings, in which like reference numerals designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 4 is a view for explaining driving patterns of electron emitters and the shapes of X-ray focuses;

FIG. 9 is a view showing a modification of the arrangement of electron emitters on an emitter substrate.

DETAILED DESCRIPTION OF THE EMBODIMENTS

The preferred embodiments of the present invention will be described below with reference to the accompanying drawings.

<First Embodiment>

Figure 1:
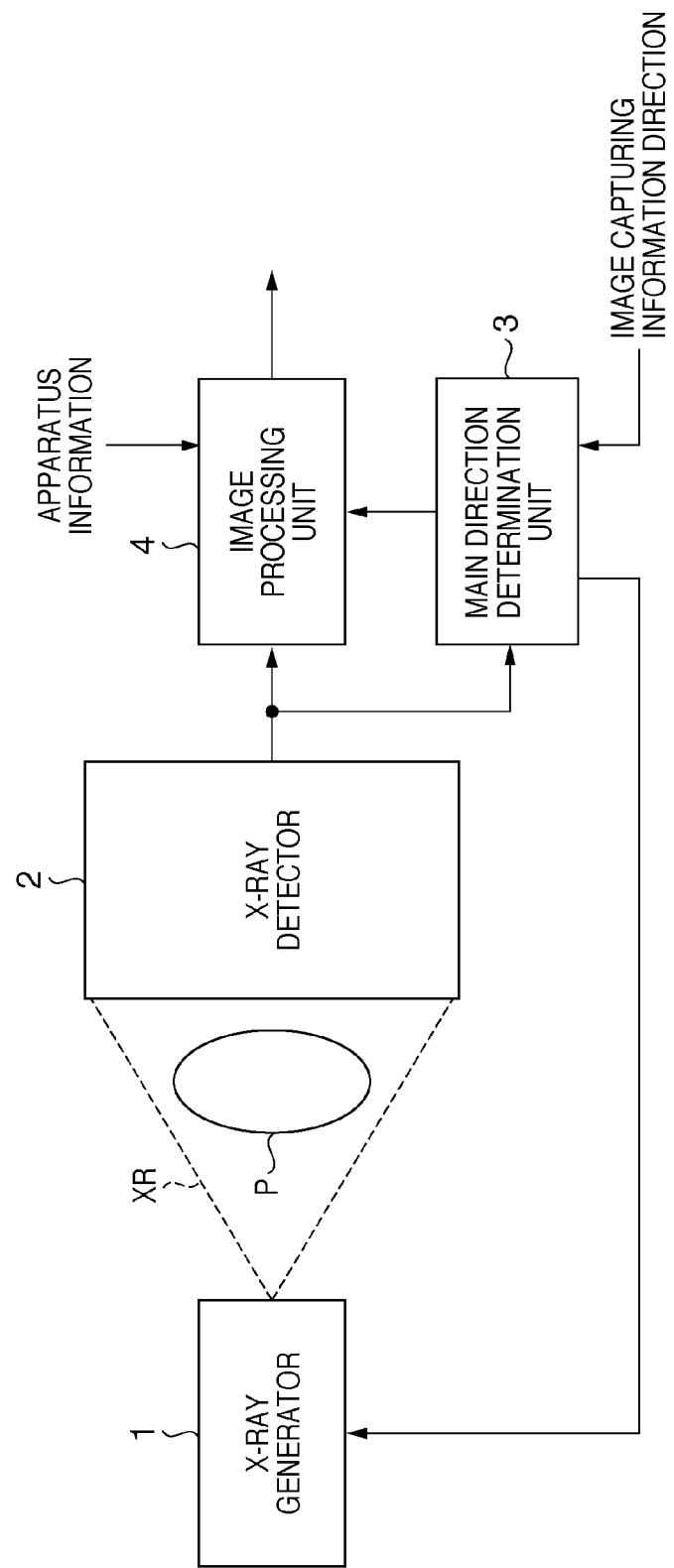
FIG. 1 is a block diagram showing an example of the basic arrangement of an X-ray imaging apparatus according to an embodiment.

FIG. 1 is a view showing the arrangement of an X-ray imaging apparatus according to the first embodiment. Referring to FIG. 1, X-rays XR emitted from an X-ray generator 1 are transmitted through an object P to be imaged, and strike an X-ray detector 2. The X-ray detector 2 is a flat panel detector for X-ray images. This detector outputs, as an image, the intensity distribution of X-rays which are transmitted through the object P and attenuated, to a main direction determination unit 3 and an image processing unit 4.

Figure 2:
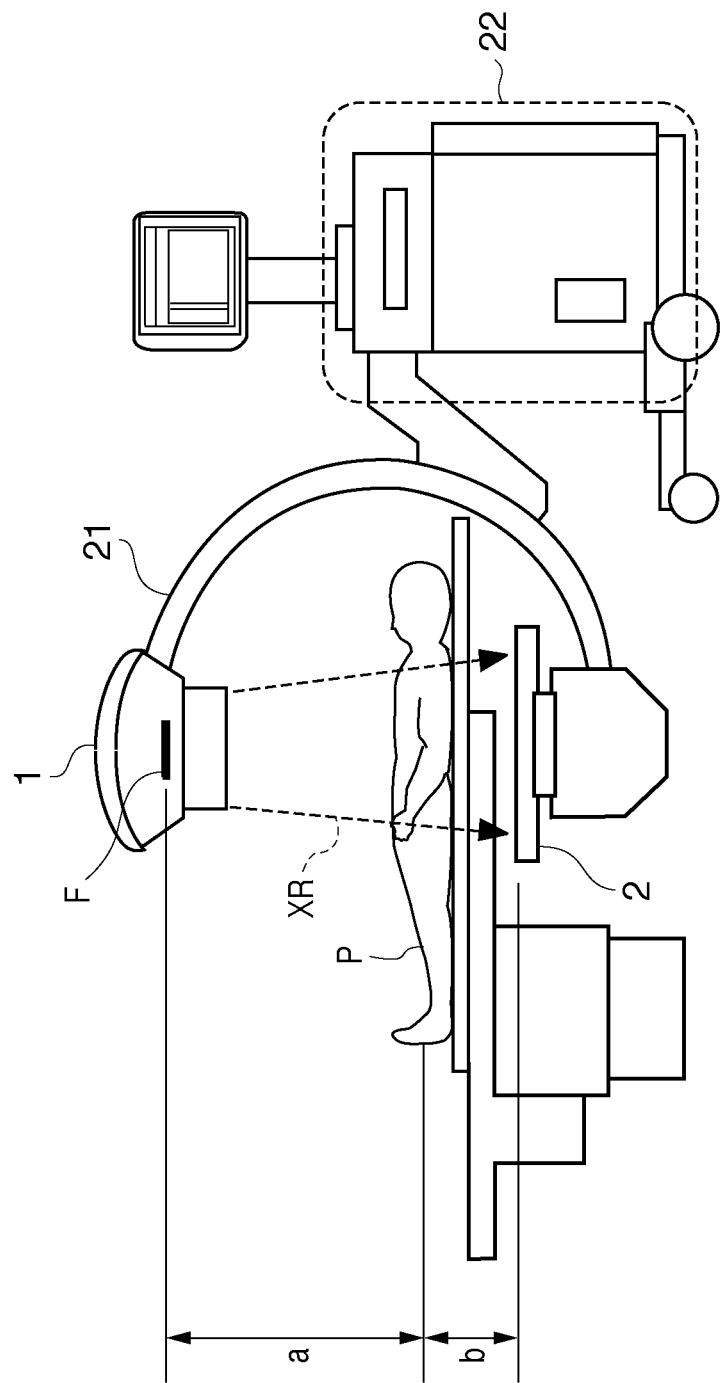
FIG. 2 is a view showing a concrete example of the X-ray imaging apparatus according to this embodiment.

A fluoroscopic radiography apparatus is a concrete example of such an imaging apparatus. A fluoroscopic radiography apparatus continuously irradiates the object P with X-rays and obtains X-ray images, thereby acquiring a moving X-ray image of the object P. FIG. 2 shows an example of this apparatus, more specifically, a fluoroscopic radiography apparatus which captures a fluoroscopic image of the patient, that is, the object P, by using the X-ray generator 1 and X-ray detector 2 which are mounted on a C-arm 21.

Referring to FIG. 2, the main direction determination unit 3 and the image processing unit 4 are implemented by a computer (not shown) housed in a controller 22 enclosed with the broken line and software.

In the first embodiment, the main direction determination unit 3 determines a main direction (to be described in detail later) by analyzing the image input from the X-ray detector 2, and controls, based on the result, the shape of an X-ray focus generated on a target electrode in the X-ray generator 1. Note that the first embodiment does not use the image processing unit 4. The image processing unit 4 will be described in the third embodiment.

Figure 3:
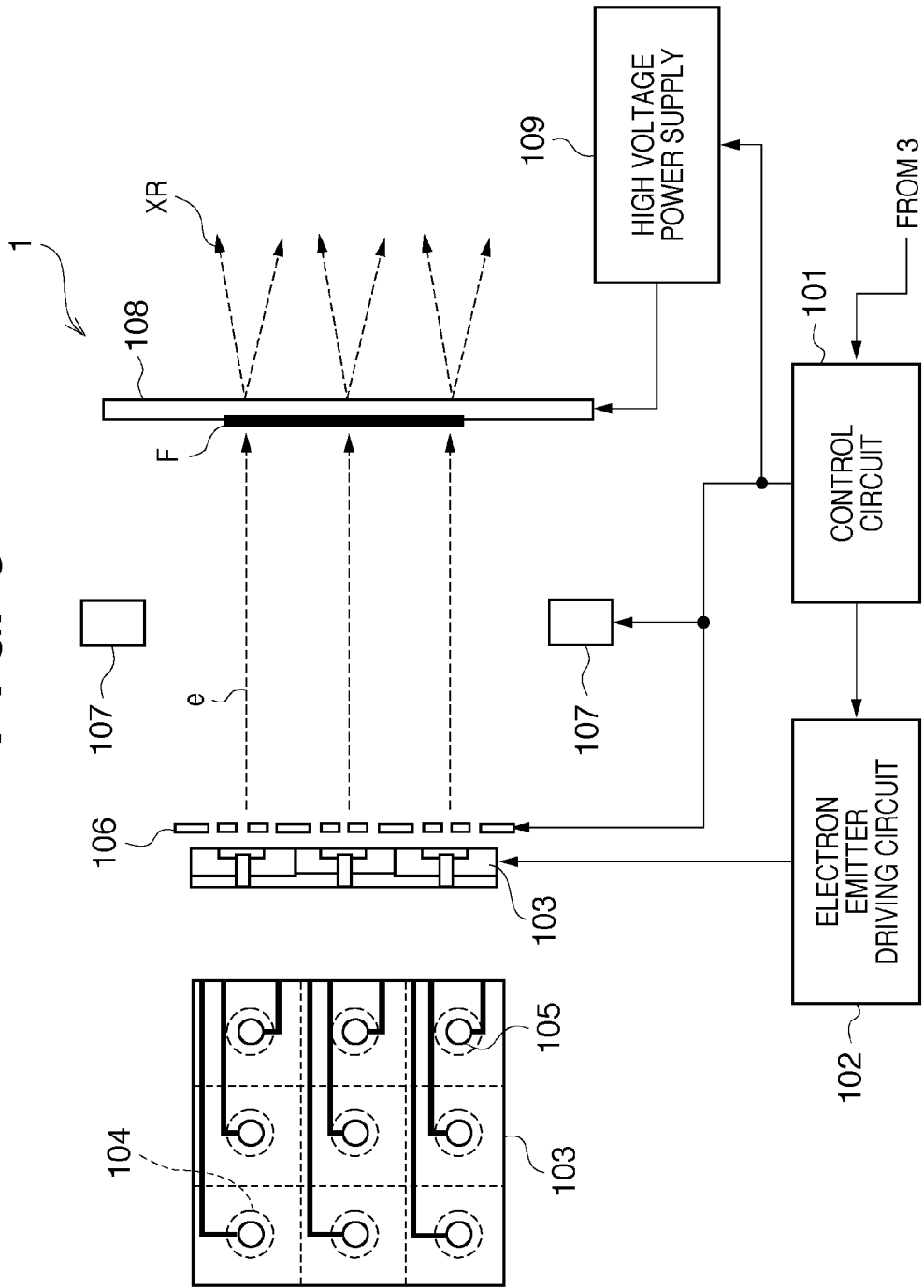
FIG. 3 is a block diagram showing an example of the basic arrangement of an X-ray generator in the X-ray imaging apparatus shown in FIG. 1.

The operation of the X-ray generator 1 will be described with reference to FIG. 3. Based on the condition input from the main direction determination 3, a control circuit 101 individually drives a plurality of electron emitters 104 arranged on an emitter substrate 103 via electrodes 105. The electrons emitted from the electron emitters 104 are formed into electron beams e by extraction electrodes 106 and lens electrodes 107. As described above, the emitter substrate 103 having the plurality of electron emitters 104 which can be individually driven, the extraction electrodes 106, and the lens electrodes 107 constitute an electron beam generating unit which generates electron beams corresponding to driven electron emitters. The electron beam e is applied onto a target electrode 108 connected to a high voltage power supply 109 to form an X-ray focus F. An X-ray XR emitted from the X-ray focus F formed on the target electrode 108 in a direction opposite to the electron beam e. The target electrode 108 generates X-rays with the irradiation position of electron beams generated by the above electron beam generating unit being an X-ray focus. The electrons emitted from the electron emitting unit constituted by the plurality of electron emitters 104 as described above are accelerated toward the target electrode 108 by the extraction electrodes 106, the lens electrodes 107, and the target electrode 108 to which a high voltage is applied. The target electrode 108 also functions as an X-ray generating unit which generates X-rays when accelerated electrons collide with the unit.

FIG. 4 is a view exemplarily showing the driving patterns of the electron emitters 104 on the emitter substrate 103 and the shapes of the X-ray focuses formed on the target electrode 108 in correspondence with the patterns. 4A to 4E in FIG. 4 each indicate that when the electron emitters 104 within the emitter substrate 103 shown on the left side which are enclosed with the thick broken line are driven, the X-ray focus with the shape shown on the right side is formed on the target electrode 108. The control circuit 101 and an electron emitter driving circuit 102 control the shape of an X-ray focus (to be also referred to as an X-ray focus shape hereinafter) formed on the target electrode by a set of X-ray focuses by individually driving/controlling the plurality of electron emitters 104. The shape of each X-ray focus can be changed by turning on or off the electrodes 105 of the electron emitters 104, as shown in FIG. 4. In addition, it suffices to change the size of an electron beam by adjusting the convergence of the electron beam by the lens electrodes 107.

Although FIG. 4 shows that electron emitters are arranged in 3×3, the number and arrangement form of electron emitters are not limited to this, and the shapes of X-ray focuses formed on the target electrode 108 are not limited to those shown in FIG. 4. For example, electron emitters can be arranged radially as shown in FIG. 9. When electron emitters are arranged as shown in FIG. 9, the intervals between the electron emitters become equal in radial directions from the center of an image. For this reason, in the pattern indicated by 4B or 4C in FIG. 4, the distributions of electron beam intensities in the radial direction can easily be made equal to each other.

The X-ray detector 2 will be described next. As shown in FIG. 1, the X-ray detector 2 is a flat panel detector which detects X-rays transmitted through the object P, converts them into a digital signal, and outputs an X-ray image. The X-ray detector 2 has X-ray detection elements arranged in a matrix. As a scheme of converting X-rays into an electrical signal, either of the following schemes can be applied to this embodiment: an indirect scheme of converting X-rays into an optical signal and then converting it into an electrical signal and a direct scheme of directly converting X-rays into an electrical signal.

The X-ray detector 2 is not limited to the above flat panel detector. For example, any device can be used as long as it outputs an X-ray image as a digital signal which is generated by causing X-rays to be transmitted through an object, such as an image intensifier or CR (Computed Radiography).

Figure 5:
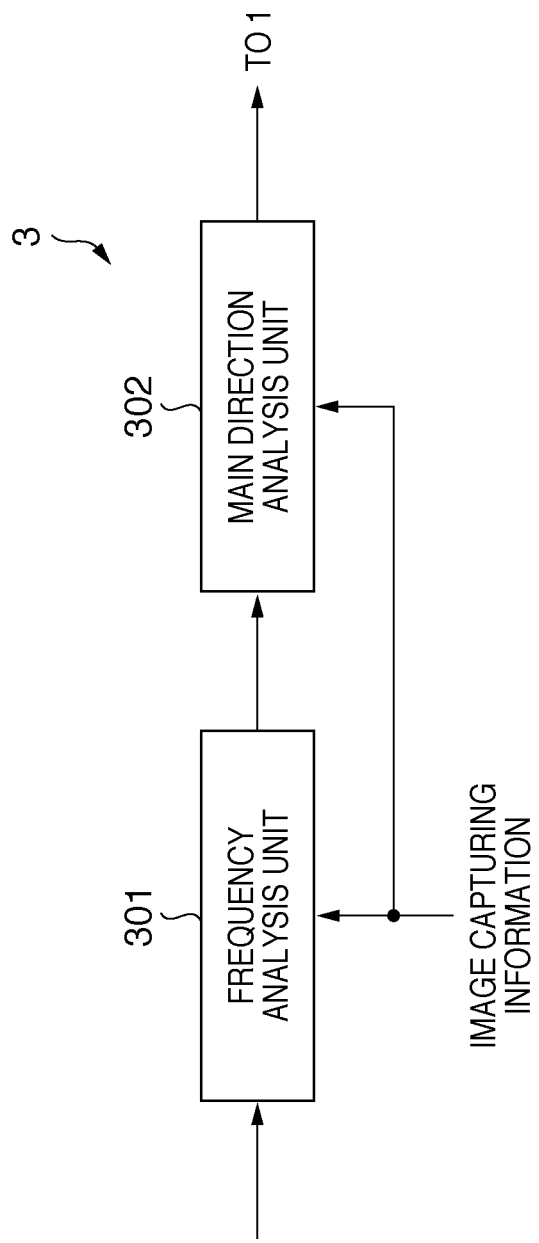
FIG. 5 is a block diagram showing an example of the arrangement of a main direction determination unit in the X-ray imaging apparatus shown in FIG. 1.

The arrangement and operation of the main direction determination unit 3 will be described next. FIG. 5 is a block diagram showing an example of the arrangement of the main direction determination unit 3. As described with reference to FIG. 2, the main direction determination unit 3 can be implemented by software in a computer, dedicated hardware, or a combination thereof.

A frequency analysis unit 301 performs frequency analysis on the X-ray image output from the X-ray detector 2 along a plurality of directions. The operation of the frequency analysis unit 301 will be exemplarily described with reference to FIG. 6.

Figure 6:
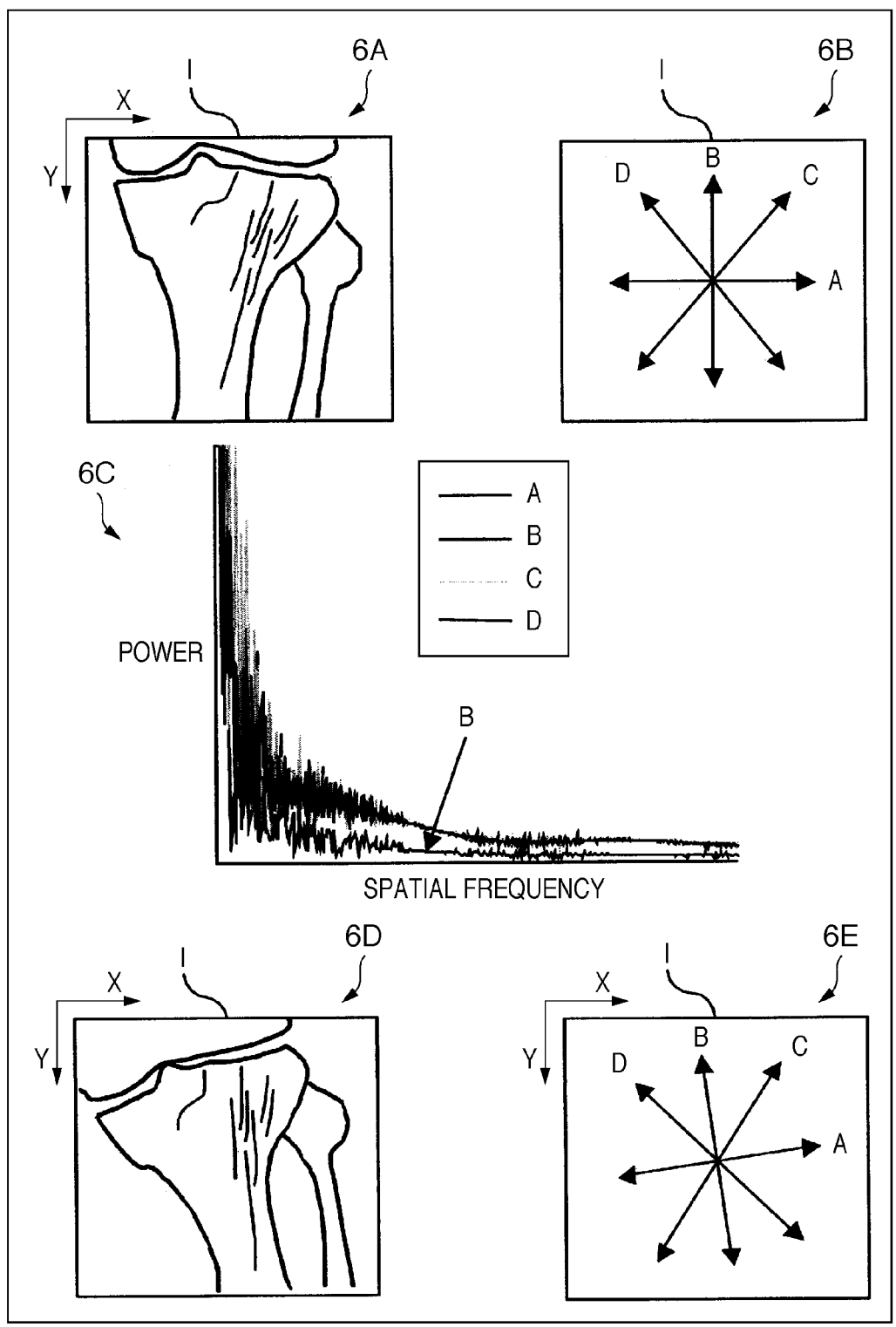
FIG. 6 is a view for explaining frequency analysis processing in the main direction determination unit.

The frequency analysis unit 301 receives an image (X-ray image) like that indicated by 6A in FIG. 6, and extracts four data strings by sampling the image data along four radial directions, that is, directions A to D indicated by 6B in FIG. 6. The frequency analysis unit 301 further calculates a frequency spectrum by performing Fourier transform for each of the data strings. 6C in FIG. 6 indicates an example of a calculated frequency spectrum. The frequency analysis unit 301 calculates the frequency power of the data string corresponding to each of the directions A to D, and outputs it as frequency power data to a main direction analysis unit 302.

The main direction analysis unit 302 performs analysis based on the frequency power data from the frequency analysis unit 301 to determine to which one of the directions A to D described above the main direction of the object on the image corresponds. In this embodiment, when the frequency power data input from the frequency analysis unit 301 is represented by $p^d$ and $d \in \{A, B, C, D\}$, the main direction analysis unit 302 determines a main direction $\eta$ according to

[Mathematical 1]

$$\eta = \arg\min_d \left( \sum_u p^d(u) \right) \quad (1)$$

where u is a spatial frequency.

$$u | ^\forall U : u > T_1 \quad \text{[Mathematical 2]}$$

According to equation (1), the main direction $\eta$ is the direction in which a frequency spectrum from which low-frequency components equal to or less than a predetermined threshold $T_1$ are excluded occupies the smallest area in a spatial frequency band U obtained by frequency decomposition. That is, in the case indicated by 6C in FIG. 6, this direction corresponds to the direction B, of the directions as analysis targets, in which included high-frequency components are smallest in amount.

Note that it suffices to set $T_1$ to a proper value in advance in accordance with the characteristics and the like of an object. It is however preferable to set, as $T_1$, a value smaller than frequency components which the structure of an object as an observation target mainly has, from which a DC component corresponding to the average luminance level of the object is excluded.

In addition, when imaging is performed under a condition that the dose of X-rays is small as in fluoroscopic radiography, in order to remove the influence of quantum noise due to a low dose of X-rays, it suffices to set a second threshold $T_2$ by which the influence of quantum noise can be avoided, and to set the range of u as follows:

$$u | ^\forall U : T_2 > u > T_1 \quad \text{[Mathematical 3]}$$

Note that the method of frequency decomposition to be used in the frequency analysis unit 301 is not limited to the above Fourier transform, and other methods, for example, discrete cosine transform, can be used as long as they can analyze the frequency components of data in the respective directions. The main direction $\eta$ obtained by the main direction determination unit 3 in the above manner is output to the control circuit 101 of the X-ray generator 1.

The control circuit 101 determines, based on the main direction $\eta$ input from the main direction determination unit 3, a driving pattern for the electron emitters 104 of the X-ray generator 1 and controls the electron emitter driving circuit 102. In this embodiment, the control circuit 101 controls the electron emitter driving circuit 102 and/or the lens electrodes 107 such that the distribution of electron beam intensities on the target electrode 108 in a direction parallel to the main direction $\eta$ becomes relatively longer than those in other directions. Assume that the main direction $\eta$ corresponds to the vertical direction of the image as in the direction B in 6B in FIG. 6, as described above. In this case, the control circuit 101 controls the driving pattern of the electron emitters 104 by the electron emitter driving circuit 102 so as to form an oblong X-ray focus shape like that indicated by 4B in FIG. 4.

According to the above control, a long X-ray focus is formed in the direction (main direction $\eta$) in which the amount of high-frequency components is small. Even if the sharpness decreases in the direction in which the amount of high-frequency components is small, the decrease in sharpness has a small influence on image quality, and necessary sharpness can be maintained. In addition, the area of an X-ray focus can be increased. This makes it possible to maintain sharpness and achieve a large current at the same time.

The above description is based on the assumption that the main direction is the direction in which the amount of high-frequency components is minimumal. However, it suffices to determine, as a main direction, a direction in which the amount of high-frequency components is maximumal, by replacing "argmin" of equation (1) with "argmax". In this case, the control circuit 101 controls the electron emitter driving circuit 102 upon selecting a driving pattern by which the size is minimized in the main direction. In each case described above, an oblong X-ray focus like that shown in 4B in FIG. 4 is formed.

In the case shown in FIG. 6, if the main direction $\eta$ is not uniquely determined because there is no difference between frequency components in the respective directions (equation 1), the main direction analysis unit 302 notifies the control circuit 101 of the corresponding information. The control circuit 101 selects a driving pattern determined in advance for this case, and controls the electron emitter driving circuit 102.

As such a driving pattern, it suffices to select a driving pattern which decreases the size of an X-ray focus in the horizontal and vertical directions, as indicated by, for example, 4E in FIG. 4. This is because the human visual sensation is higher for a decrease in sharpness in the horizontal and vertical directions than in the diagonal direction.

Figure 8:
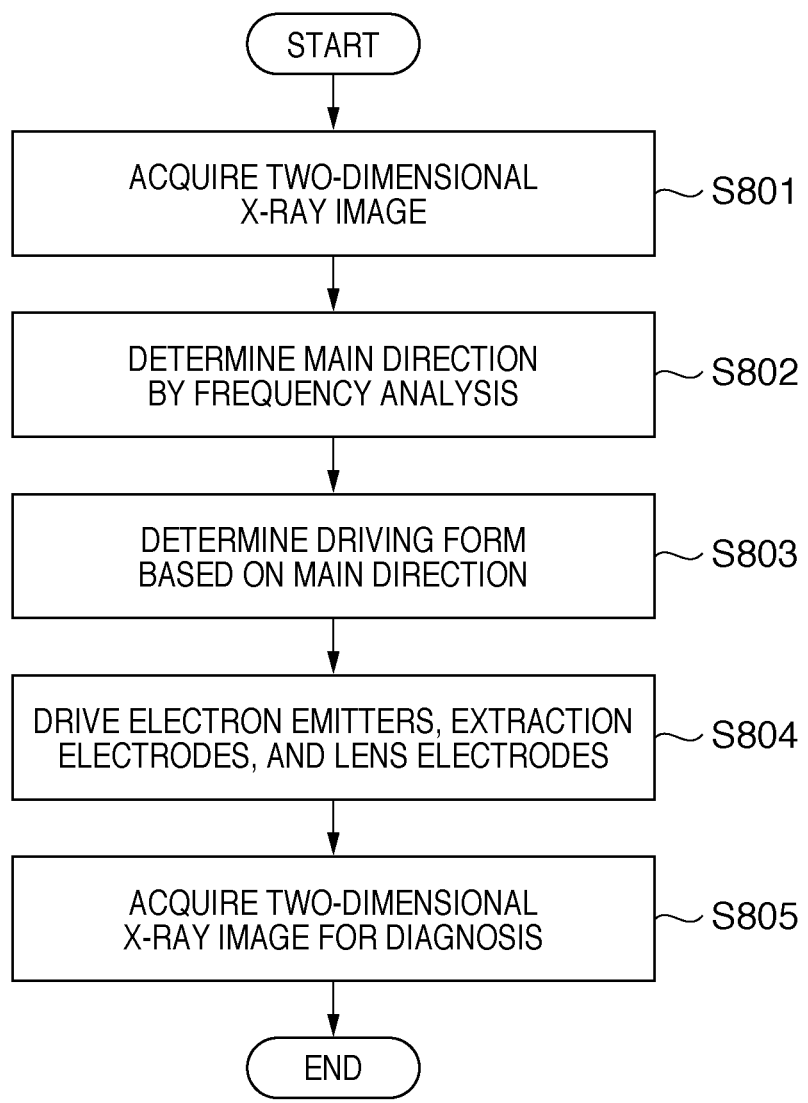
FIG. 8 is a flowchart for explaining X-ray imaging processing according to the first embodiment.

FIG. 8 is a flowchart for explaining X-ray imaging processing in the first embodiment. In step S801, the main direction determination unit 3 acquires an X-ray image from the X-ray detector 2. In step S802, the main direction determination unit 3 performs frequency analysis on the X-ray image to determine the main direction of the image. The determined main direction is notified to the control circuit 101 of the X-ray generator 1. In step S803, the control circuit 101 determines, for example, selective driving for electron emitters and driving patterns for the extraction electrodes 106 and lens electrodes 107 so as to broaden more the electron beam intensity distribution in the main direction notified from the main direction determination unit 3 than in other directions. In step S804, these arrangements are actually controlled to be driven. By such driving of the X-ray generator 1, a two-dimensional X-ray image is acquired from the X-ray detector 2 and provided as an image for diagnosis (step S805).

As described above, the first embodiment analyzes the frequency characteristics of an acquired image, and forms an X-ray focus so as to elongate it in a direction in which the amount of high-frequency components is small. That is, the main direction determination unit 3, the control circuit 101, and the like control the driving of a plurality of electron emitters in accordance with the frequency characteristics of the image, and change the emission distribution pattern of electrons emitted by the emitter substrate 103 as an electron emitting unit. Since the target electrode 108 generates X-rays corresponding to this emission distribution pattern, the object P is irradiated with an X-ray pattern corresponding to the emission distribution pattern. This makes it possible to obtain a large current as a whole without greatly influencing sharpness in the direction in which the amount of high-frequency components is large.

Although an X-ray image is acquired in steps S801 and S805 in the flowchart of FIG. 8, it suffices to set a proper X-ray irradiation dose for each process. For example, it suffices to set the X-ray irradiation amount in step S801 to a level that is necessary for frequency analysis. In order to reduce the X-ray exposure dose of the object, the X-ray irradiation dose in step S801 may be set to be smaller than in step S805.

<Second Embodiment>

In the first embodiment described above, a main direction is determined based on frequency analysis on the image captured by X-ray imaging. Another embodiment may be configured to determine a main direction based on an external input. This embodiment will be described below.

In the second embodiment, a main direction determination unit 3 inputs image capturing information from the outside in addition to an X-ray image from an X-ray detector 2. In this case, the image capturing information is information about an object to be imaged or information about the main direction of the object. For example, in a medical imaging apparatus, image capturing information includes information indicating a specific region as an object to be imaged, for example, a chest region, extremity region, or abdominal region, information indicating a visual line direction, and information indicating in which direction an object extends on an image when a region to be imaged is an extremity region.

When the main direction determination unit 3 is implemented as software in a computer as described with reference to FIG. 2, the unit can be configured to allow an operator to directly input image capturing information by using an input device, for example, a keyboard or mouse (not shown). When the main direction determination unit 3 is implemented by dedicated hardware, it suffices to input image capturing information in advance by using a button or the like set for each information capturing target.

Alternatively, when an imaging apparatus is a medical imaging apparatus, the apparatus can be configured to receive image capturing information online from a radiation information system instead of directly inputting by operation by an operator.

The operation of the main direction determination unit 3 in this embodiment will be described below by exemplifying a case in which a region to be imaged is a knee joint as shown in FIG. 6.

In the second embodiment, as shown in FIG. 5, image capturing information is input to a frequency analysis unit 301. Assume that in this case, the image capturing information represents the type and direction of a region to be imaged, and an X-ray image indicates a knee joint imaged in a slightly tilted state as exemplified by 6D in FIG. 6. The frequency analysis unit 301 holds, in a memory (not shown), the direction of frequency analysis associated in advance with a region to be imaged. Assume that if the region to be imaged is the skeletal system of the extremities, the four directions (A to D) indicated by 6B in FIG. 6 are selected.

The frequency analysis unit 301 rotates the four directions indicated by 6B in FIG. 6 to the four directions indicated by 6E in FIG. 6 based on "direction" contained in the input image capturing information. Note that "direction" contained in the image capturing information is, for example, the direction (angle) of an image capturing target which is input by the operator using the keyboard. With regard to the four directions indicated by 6E in FIG. 6, four data strings are generated as in the first embodiment, and a frequency spectrum is calculated. The subsequent operation of the main direction determination unit 3 is the same as that in the first embodiment, and hence a repetitive description will be omitted.

Note that when a control circuit 101 selects a driving pattern, since the object is in a slightly rotated state unlike in the first embodiment, it is possible that in the second embodiment, a main direction η does not accurately coincide with any of the patterns exemplified by 4A to 4E in FIG. 4. In this case, a driving pattern which is most similar to any of the patterns is selected. Alternatively, the control circuit 101 may adjust driving currents for electron emitters 104 such that the electron beam intensity distribution formed on a target electrode 108 is elongated in the main direction. Effects similar to those of the first embodiment can be obtained by performing control to make the emission distribution pattern of electrons emitted by an emitter substrate 103 have an electron beam intensity distribution elongated in the main direction. This makes it possible to achieve a large current as a whole without greatly influencing sharpness in the direction in which the amount of high-frequency components is large.

In the second embodiment, image capturing information such as a region to be imaged and a direction is input, and frequency analysis is performed by using the image capturing information to determine a main direction. With this operation, if it is known that an object has a characteristic in a specific direction, it is possible to capture an image of the object without decreasing the sharpness corresponding to the characteristic.

<Third Embodiment>

The first and second embodiments are configured to change the shape of an X-ray focus in accordance with the main direction of an object to be imaged and secure the sharpness of an image in accordance with the object. The third embodiment will exemplify an X-ray imaging apparatus which also secures sharpness in a direction in which an X-ray focus is long.

The third embodiment is characterized in that an image processing unit 4 shown in FIG. 1 performs sharpening processing (frequency enhancement processing) for an input X-ray image based on a main direction η determined by a main direction determination unit 3.

Figure 7:
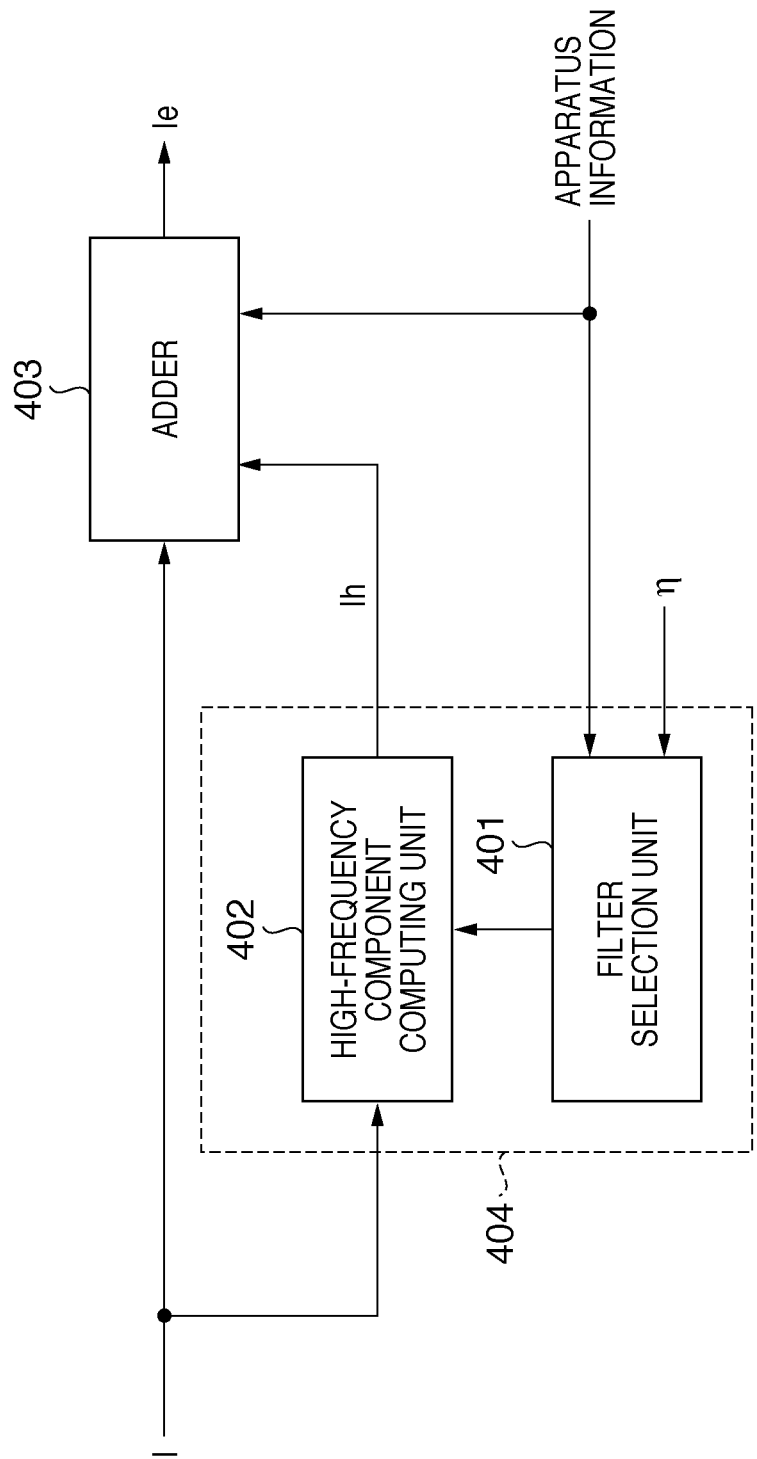
FIG. 7 is a block diagram showing an example of the arrangement of an image processing unit in the X-ray imaging apparatus shown in FIG. 1.

FIG. 7 is a block diagram showing the arrangement of the image processing unit 4. A high-frequency component computing unit 402 receives an X-ray image I input from an X-ray detector 2. A filter selection unit 401 receives the main direction η input from the main direction determination unit 3, and selects a high-frequency component extraction filter corresponding to the main direction. The high-frequency component computing unit 402 extracts a high-frequency component Ih by performing convolution by using the filter selected for the input image I, and outputs the component to an adder 403. The adder 403 adds the input image I and the high-frequency component Ih and outputs a sharpened image Ie.

The operation of each unit will be described in detail below based on the examples used in the first embodiment. The filter selection unit 401 selects an optimal filter G from four types of filters based on which one of the directions indicated by 6B in FIG. 6 is the input main direction η, and outputs the filter to the high-frequency component computing unit 402. Note that in this embodiment, the main direction η is a direction in which the amount of high-frequency components is small.

[Mathematical 4]

$$G = \begin{cases} \begin{bmatrix} 0 & 1/3 & 0 \\ 0 & 1/3 & 0 \\ 0 & 1/3 & 0 \end{bmatrix} : \eta = (B) \\ \begin{bmatrix} 0 & 0 & 0 \\ 1/3 & 1/3 & 1/3 \\ 0 & 0 & 0 \end{bmatrix} : \eta = (A) \\ \begin{bmatrix} 0 & 0 & 1/3 \\ 0 & 1/3 & 0 \\ 1/3 & 0 & 0 \end{bmatrix} : \eta = (C) \\ \begin{bmatrix} 1/3 & 0 & 0 \\ 0 & 1/3 & 0 \\ 0 & 0 & 1/3 \end{bmatrix} : \eta = (D) \end{cases} \quad (2)$$

The high-frequency component computing unit 402 obtains the high-frequency component Ih by performing convolution for the input image I using the filter G, and outputs the obtained component to the adder 403. The adder 403 adds the weighted high-frequency component Ih to the input image I. The above processing is therefore expressed by equations (3) and (4) given below:

[Mathematical 5]

$$Ie = I + w \cdot Ih \quad (3)$$

$$Ih = I - I*G \quad (4)$$

Note that "*" represents convolution and "w" represents a weighting factor, which is stored in a memory (not shown) which can be read by the image processing unit 4. It suffices to determine one value as the value of w in advance by an experiment or the like or to determine optimal values in advance in accordance with regions to be imaged and select one of the values based on input image capturing information as described in the second embodiment.

Elongating an X-ray focus shape in a direction in which the amount of high-frequency components is small (corresponding to the direction B in 6B in FIG. 6 in the above case) will selectively enhance a high-frequency component in the direction by image processing even with a decrease in sharpness in the direction. That is, the third embodiment performs frequency enhancement processing for a two-dimensional X-ray image so as to enhance high-frequency components in the main direction relative to other directions, and hence corrects the anisotropy of sharpness.

<Fourth Embodiment>

Image processing by the image processing unit 4 described in the third embodiment is not limited to the above method, and can take various forms. For example, as exemplified in the second embodiment, the present invention can be applied to even a case in which an object to be imaged is tilted, and its direction is at an arbitrary angle. An example of an image processing unit 4 which can cope with a main direction at an arbitrary angle will be described below.

In the fourth embodiment, a filter selection unit 401 and a high-frequency component computing unit 402 are implemented by the method disclosed in the following non-patent reference. This method can rotate a filter through an arbitrary angle. Since the method is described in detail in this reference, a repetitive description will be omitted. Operation as the function of a processing block 404 as a combination of the filter selection unit 401 and the high-frequency component computing unit 402 will be described below with reference to FIG. 7.

[Non-patent Reference] W. T. Freeman and E. H. Adelson, "The design and use of steerable filters", IEEE Trans. Pattern Analysis and Machine Intelligence, Vol. 13 NO. 9, pp. 891-906, 1991.

The processing block 404 calculates a high-frequency component Ih based on a main direction η as follows. Note that the main direction η in the fourth embodiment represents an arbitrary angle ([degree]). Note that in this embodiment, the main direction η is a direction in which the amount of high-frequency components is small.

[Mathematical 6]

$$Ih = \cos(\eta)(I*G_1^0) + \sin(\eta)(I*G_1^{90}) \quad (5)$$

The high-frequency component Ih obtained by equation (5) is an enhanced component in the main direction η. Processing this component by equation (3) can increase the sharpness in this direction.

Note that $G_1^0$ and $G_1^{90}$ represent filters corresponding to first-order derivatives in the horizontal and vertical directions in a Gaussian distribution, which are calculated by the following equations in this embodiment:

[Mathematical 7]

$$G_1^0 = -\frac{x}{\sigma^2} x e^{\frac{x^2}{2\sigma^2}} \quad (6)$$

$$G_1^{90} = G_1^{0T}$$

In this case, $G_1^{0T}$ is the transposition of $G_1^0$. Actual filter coefficients can be calculated by determining x in equation (6) according to the following inequality:

[Mathematical 8]

$$-\left[\frac{N}{2}\sigma\right] \le x \le \left[\frac{N}{2}\sigma\right]; x \in z \quad (7)$$

In this case, N is a basic filter size, and Z is a set of integers. If N is 5 and a standard deviation σ is 1, filter coefficients are obtained as follows:

[Mathematical 9]

$$G_1^0 = [0.2707 \quad 0.6065 \quad 0 \quad -0.6065 \quad -0.2707] \quad (8)$$

$$G_1^{90} = \begin{bmatrix} 0.2707 \\ 0.6065 \\ 0 \\ -0.6065 \\ -0.2707 \end{bmatrix}$$

It is preferable that proper values can be selected in advance as a filter size and the standard deviation σ based on the size of an X-ray focus F, the MTF of an X-ray detector 2, the positional relationship between the X-ray focus F, an object P to be imaged, and the X-ray detector 2, and the like. Note that MTF stands for modulation transfer function, which is an index of sharpness.

That is, the filter selection unit 401 stores filters calculated from a plurality of sizes and standard deviations in a memory (not shown) in advance. It suffices to select a filter having a larger size or larger standard deviation σ to enhance the high frequency enhancement effect as the X-ray focus F increases or a ratio b/a between a distance a between the X-ray focus F and the object P and a distance b between the X-ray detector 2 and the object P increases.

Alternatively, high frequency enhancement can be implemented by increasing w in an adder 403. In addition, it suffices to store the MTF of the X-ray detector 2, the distance ratio a/b, and the like described above in a memory in the X-ray imaging apparatus in advance or to acquire such data by sensing the vertical movement of a table on which the object P is placed during imaging or of a C-arm 21 by using a sensor. Such data is input as apparatus information to an image processing unit 4, as shown in FIG. 7.

As described above, the fourth embodiment can enhance a high-frequency component in an arbitrary direction. Even if, therefore, the direction in which the sharpness decreases due to the anisotropic shape of an X-ray focus is an arbitrary angle, a corresponding correction can be made.

As described above, according to each embodiment described above, an electron emitter driving circuit 102 which can individually drive a plurality of electron emitters 104 which emit electron beams and a control circuit 101 can form an X-ray focus having an arbitrary shape on a target electrode 108. This makes it possible to generate an image having sharpness in a specific direction in imaging operation using an X-ray generator. Therefore, a direction in which the amount of high-frequency components is minimum is determined as a main direction, and an X-ray focus shape extending in a direction along the main direction can be formed. Elongating the X-ray focus in a direction in which the influence of sharpness is low can prevent a decrease in sharpness and achieve an X-ray focus with a large area. That is, it is possible to supply the amount of electrons (current), large enough to maintain image quality, to the target electrode while keeping sharpness.

The X-ray imaging apparatus according to each embodiment described above controls the shape of an X-ray focus, in accordance with the main direction determined by the main direction determination unit 3 from the two-dimensional X-ray image obtained by the X-ray detector 2. This makes it possible to improve the image quality of a captured image by achieving a large current while maintaining sharpness in accordance with an image capturing target.

According to the X-ray imaging apparatuses of the third and fourth embodiments, even if the resolution lowers in a given direction depending on an X-ray focus having an arbitrary shape, it is possible to suppress the influence of the decrease in resolution on diagnosis by making the image processing unit 4 perform sharpening processing in the direction.

[Other Embodiments]

The present invention incorporates a case in which programs of software are directly or remotely supplied to a system or apparatus to cause the computer of the system or apparatus to read out and execute the program codes, thereby implementing the functions of the above embodiments. In this case, the supplied programs are computer programs corresponding to the flowcharts shown in the accompanying drawings in the embodiments.

The program codes themselves which are installed in the computer to allow the computer to implement the functions/processing of the present invention also implement the present invention. That is, the present invention incorporates the computer programs themselves for implementing the functions/processing of the present invention.

In this case, each program may take any form, for example, an object code, a program executed by an interpreter, and script data supplied to an OS, as long as it has the function of the program.

A computer-readable storage medium for supplying the computer programs includes, for example, a floppy® disk, hard disk, optical disk, magnetooptical disk, MO, CD-ROM, CD-R, CD-RW, magnetic tape, nonvolatile memory card, ROM, DVD (DVD-ROM or DVD-R), or the like.

In addition, methods of supplying the programs include the following. A client computer connects to a homepage on the Internet by using a browser to download each computer program of the present invention from the homepage into a recording medium such as a hard disk. In this case, the program to be downloaded may be a compressed file containing an automatic install function. Alternatively, the programs can be supplied by dividing the program codes constituting each program of the present invention into a plurality of files, and downloading the respective files from different homepages. That is, the present invention also incorporates a WWW server which allows a plurality of users to download program files for causing the computer to execute the functions/processing of the present invention.

In addition, the functions/processing of the present invention can be implemented by encrypting the programs of the present invention, storing the encrypted data in storage media such as CD-ROMs, and distributing them to users. In this case, users who satisfy a predetermined condition are allowed to download key information for decryption from a homepage through the Internet. Executing the encrypted programs using the key information allows a computer to install the programs.

The functions of the above embodiments are implemented by making the computer execute the readout programs. In addition, the functions of the above embodiments may also be implemented by making the computer operate in cooperation with the OS or the like running on the computer based on the instructions of the programs. In this case, the OS or the like performs part or all of actual processing to implement the functions of the above embodiments.

Part or all of the functions of the above embodiments may also be implemented by writing the programs read out from the recording medium in the memory of a function expansion board inserted into the computer or a function expansion unit connected to the computer. In this case, after the programs are written in the function expansion board or the function expansion unit, the CPU or the like of the function expansion board or function expansion unit performs part or all of actual processing based on the instructions of the programs.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-032351, filed Feb. 13, 2008 which is hereby incorporated by reference herein in its entirety.

The invention claimed is:

1. An X-ray imaging apparatus comprising:
an electron beam generating unit, having a plurality of electron emitters, configured to generate an electron beam corresponding to driven electron emitters;
a target electrode which generates X-rays with an irradiation position of an electron beam generated by the electron beam generating unit being an X-ray focus;
a detection unit configured to generate a two-dimensional X-ray image by detecting X-rays generated from the target electrode;
a driving control unit configured to control an X-ray focus shape formed by a set of X-ray focuses on the target electrode by individually controlling driving of the plurality of electron emitters; and
a determination unit configured to determine the X-ray focus shape which the driving control unit is to form on the target electrode, based on the two-dimensional X-ray image detected by the detection unit,
wherein the driving control unit includes a main direction determination unit for determining, as a main direction, a direction in which an amount of high-frequency components becomes minimum, by performing frequency analysis on the two-dimensional X-ray image in a plurality of directions, and determines the X-ray focus shape to be formed on the target electrode, based on the main direction.

2. The X-ray imaging apparatus according to claim 1, further comprising an input unit configured to input image capturing information including information indicating a region as an image capturing target,
  wherein the main direction determination unit selects a plurality of directions in which the frequency analysis is to be performed, based on the region to be imaged which is indicated by the image capturing information.

3. The X-ray imaging apparatus according to claim 2, wherein
  the image capturing information further includes information indicating a target direction on the two-dimensional X-ray image, and
  the main direction determination unit rotates a plurality of directions, selected based on the image capturing target, in which frequency analysis is to be performed, on the basis of information indicating the target direction.

4. The X-ray imaging apparatus according to claim 1, further comprising a lens electrode provided between the electron beam generating unit and the target electrode to form the electron beam,
  wherein the driving control unit controls driving of the plurality of electron emitters and driving of the lens electrode such that a distribution of electron beam intensities on the target electrode in a direction parallel to the main direction becomes relatively longer than distributions in other directions.

5. The X-ray imaging apparatus according to claim 1, further comprising an image processing unit configured to perform frequency enhancement processing for a two-dimensional X-ray image detected by the detection unit,
  wherein the image processing unit enhances a high-frequency component in the main direction relative to other directions.

6. An X-ray generator which generates X-rays, comprising:
  an electron beam generating unit having a plurality of electron emitters configured to generate an electron beam corresponding to driven electron emitters;
  a target electrode which generates X-rays with an irradiation position of an electron beam generated by the electron beam generating unit being an X-ray focus;
  a driving control unit configure to control an X-ray focus shape formed by a set of X-ray focuses on the target electrode by individually controlling driving of the plurality of electron emitters; and
  a determination unit configured to determine the X-ray focus shape which the driving control unit is to form on the target electrode, based on a two-dimensional X-ray image generated by detecting X-rays generated from the target electrode,
  wherein the driving control unit includes a main direction determination unit for determining, as a main direction, a direction in which an amount of high-frequency components becomes minimum, by performing frequency analysis on the two-dimensional X-ray image in a plurality of directions, and determines the X-ray focus shape to be formed on the target electrode, based on the main direction.

7. A control method for an X-ray imaging apparatus including an electron beam generating unit, having a plurality of electron emitters, for generating an electron beam corresponding to driven electron emitters, a target electrode which generates X-rays with an irradiation position of an electron beam generated by the electron beam generating unit being an X-ray focus, and a detection unit for generating a two-dimensional X-ray image by detecting X-rays generated from the target electrode, the method comprising:
  controlling an X-ray focus shape formed by a set of X-ray focuses on the target electrode by individually controlling driving of the plurality of electron emitters;
  determining the X-ray focus shape which is to be formed on the target electrode, based on the two-dimensional X-ray image detected by the detection unit;
  determining, as a main direction, a direction in which an amount of high-frequency components becomes minimum, by performing frequency analysis on the two-dimensional X-ray image in a plurality of directions; and
  determining the X-ray focus shape to be formed on the target electrode, based on the main direction.

8. A computer readable storage medium storing thereon a program which causes a computer to execute a control method for an X-ray imaging apparatus, according to claim 7.

9. A control method for an X-ray generator including an electron beam generating unit having a plurality of electron emitters configured to generate an electron beam corresponding to drive electron emitters, and a target electrode which generates X-rays with an irradiation position of an electron beam generated by the electron beam generating unit being an X-ray focus, the method comprising:
  controlling an X-ray focus shape formed by a set of X-ray focuses on the target electrode by individually controlling driving of the plurality of electron emitters
  determining the X-ray focus shape which is to be formed on the target electrode, based on a two-dimensional X-ray image generated by detecting X-rays generated from the target electrode;
  determining, as a main direction, a direction in which an amount of high-frequency components becomes minimum, by performing frequency analysis on the two-dimensional X-ray image in a plurality of directions; and
  determining the X-ray focus shape to be formed on the target electrode, based on the main direction.

10. A computer-readable storage medium storing thereon a program which causes a computer to execute a control method for an X-ray generator, according to claim 9.

11. An X-ray imaging apparatus comprising:
  an electron beam generating unit, having a plurality of electron emitters which are two- dimensionally arranged, configured to generate an electron beam corresponding to driven electron emitters;
  a target electrode which generates X-rays with an irradiation position of an electron beam generated by the electron beam generating unit;
  a lens electrode provided between the electron beam generating unit and the target electrode to form the electron beam;
  a determination unit configured to determine an X-ray focus shape and size to be formed on the target electrode; and
  a driving control unit configured to control an X-ray focus shape formed by a set of X-ray focuses on the target electrode by individually controlling driving of the plurality of electron emitters and control driving of the lens electrode to form the determined X-ray focus shape and size.

12. The X-ray imaging apparatus according to claim 11, wherein the determination unit determines the X-ray focus shape which the driving control unit is to form on the target electrode, based on a two-dimensional X-ray image generated based on X-rays detected by detection unit which detects X-rays generated from the target electrode.

13. The X-ray imaging apparatus according to claim 12, wherein the determination unit determines by performing a frequency analysis on the two-dimensional X-ray image detected by the detection unit in a plurality of directions, an X-ray focus shape to be formed on the target electrode, such that distribution of electron beam intensities in a main direction in which the amount of high frequency components is minimal, is relatively longer than those in other directions.

14. The X-ray imaging apparatus according to claim 12, wherein the determination unit determines, as a main direction, a direction in which an amount of high-frequency components becomes minimum, based on a frequency analysis, and determines the X-ray focus shape to be formed on the target electrode, based on the main direction.

15. The X-ray imaging apparatus according to claim 14, further comprising an input unit configured to input image capturing information including information indicating a region as an image capturing target,
wherein the determination unit selects a plurality of directions in which the frequency analysis is to be performed, based on the region to be imaged which is indicated by the image capturing information.

16. The X-ray imaging apparatus according to claim 15, wherein
the image capturing information further includes information indicating a target direction on the two-dimensional X-ray image, and
the determination unit rotates a plurality of directions, selected based on the image capturing target, in which frequency analysis is to be performed, on the basis of information indicating the target direction.

17. The X-ray imaging apparatus according to claim 14, wherein the driving control unit controls driving of the plurality of electron emitters and driving of the lens electrode such that a distribution of electron beam intensities on the target electrode in a direction parallel to the main direction becomes relatively longer than distributions in other directions.

18. The X-ray imaging apparatus according to claim 14, further comprising an image processing unit configured to perform frequency enhancement processing for a two-dimensional X-ray image detected by the detection unit,
wherein the image processing unit enhances a high-frequency component in the main direction relative to other directions.

19. A control method for an X-ray imaging apparatus including an electron beam generating unit having a plurality of electron emitters for generating an electron beam corresponding to driven electron emitters which are two-dimensionally arranged, a target electrode which generates X-rays with an irradiation position of an electron beam generated by the electron beam generating unit being an X-ray focus, and a lens electrode provided between the electron beam generating unit and the target electrode to form an electron beam, the method comprising:
determining an X-ray focus shape and size to be formed on the target electrode;
controlling an X-ray focus shape formed by a set of X-ray focuses on the target electrode by individually controlling driving of the plurality of electron emitters; and
controlling driving of the lens electrode to form the determined X-ray focus shape and size.

20. A computer readable storage medium storing thereon a program which causes a computer to execute a control method for an X-ray imaging apparatus, according to claim 19.

* * * * *